United States Patent
Hayashi

(10) Patent No.: US 8,405,048 B2
(45) Date of Patent: Mar. 26, 2013

(54) FLUORESCENCE DETECTION DEVICE AND FLUORESCENCE DETECTION METHOD

(75) Inventor: Hironori Hayashi, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 341 days.

(21) Appl. No.: 12/866,130

(22) PCT Filed: Feb. 4, 2009

(86) PCT No.: PCT/JP2009/000423
§ 371 (c)(1),
(2), (4) Date: Aug. 4, 2010

(87) PCT Pub. No.: WO2009/098867
PCT Pub. Date: Aug. 13, 2009

(65) Prior Publication Data
US 2010/0327184 A1   Dec. 30, 2010

(30) Foreign Application Priority Data

Feb. 7, 2008   (JP) .................. 2008-027284

(51) Int. Cl.
*G01J 1/58* (2006.01)
(52) U.S. Cl. ..................... 250/458.1; 356/318
(58) Field of Classification Search .............. 250/458.1, 250/459.1; 356/300, 311, 317, 318
See application file for complete search history.

(56) References Cited

U.S. PATENT DOCUMENTS

| 5,017,008 A | 5/1991 | Akiyama |
| 5,372,783 A | 12/1994 | Lackie |
| 2005/0046834 A1 | 3/2005 | Gilby |
| 2008/0024758 A1* | 1/2008 | Tabata ............ 356/39 |

FOREIGN PATENT DOCUMENTS

| EP | 0 538 551 A2 | 4/1993 |
| JP | 01-109245 A | 4/1989 |
| JP | 01-242939 A | 9/1989 |
| JP | 05-034261 A | 2/1993 |
| JP | 05-119035 A | 5/1993 |
| JP | 07-500191 A | 1/1995 |
| JP | 10-221244 A | 8/1998 |
| JP | 2821191 B2 | 11/1998 |
| JP | 2004-530868 A | 10/2004 |

OTHER PUBLICATIONS

Beckman Coulter, Inc., "Introduction to Principles of FCM-V", Japanese website, http://www.bc-cytometry.com/FCM/fcmprinciple_5.html#5-1, http://www.bc-cytometry.com/FCM/fcmprinciple_6-1.html, searched on Nov. 28, 2007.

* cited by examiner

*Primary Examiner* — Mark R Gaworecki
(74) *Attorney, Agent, or Firm* — Global IP Counselors, LLP

(57) ABSTRACT

A fluorescence detection device includes a flow cell body including a flow channel through which a measurement object flows, a laser light source unit that irradiates, with a laser beam, the measurement object passing through a measurement point in the flow channel, a light-receiving unit that receives fluorescence emitted from the measurement object irradiated with the laser beam and outputs a light-reception signal, and a processing unit that outputs an output value of fluorescence intensity based on the light-reception signal outputted by the light-receiving unit. The flow cell body has a lens provided on a surface thereof so as to traverse an optical path of the laser beam.

13 Claims, 5 Drawing Sheets

FLUORESCENCE DETECTION DEVICE AND FLUORESCENCE DETECTION METHOD

CROSS-REFERENCE TO RELATED APPLICATIONS

This U.S. National stage application claims priority under 35 U.S.C. §119(a) to Japanese Patent Application No. 2008-027284, filed in Japan on Feb. 7, 2008, the entire contents of which are hereby incorporated herein by reference.

TECHNICAL FIELD

The present invention relates to a fluorescence detection device and a fluorescence detection method of measuring fluorescence emitted from a measurement object by irradiation with a laser beam.

BACKGROUND ART

A flow cytometer used in medical and biological fields includes a fluorescence detection device that receives fluorescence emitted from a fluorochrome attached to a measurement object by irradiation with a laser beam to identify the type of the measurement object. Particularly, in recent years, attempts have been made to perform fluorescence measurement using fluorochromes to examine intracellular local information such as proteins.

In order to examine intracellular local information, it is necessary to achieve higher measurement resolution than ever before.

As described in the online article "Introduction to Principles of FCM-V," which could be found at http://www.bc-cytometry.com/FCM/fcmprinciple_5.html#5-1 and http://www.bc-cytometry.com/FCM/fcmprinciple_6-1.html on Nov. 28, 2007, a currently-used flow cytometer includes a flow cell (flow cell body). The flow cell is a hollow chamber made of quartz and elongated and having a rectangular cross-section. The flow cell transmits a laser beam and is used to irradiate cells contained in a sample with a laser beam. When passing through a measurement point in the flow cell, a measurement object is irradiated with a laser beam passing through the flow cell, and fluorescence is detected by a detection system provided separately from the flow cell.

The aforementioned online article "Introduction to Principles of FCM-V" describes the following. The light intensity of a laser beam has a Gaussian distribution. The laser beam is focused to an elliptical cross-section to increase its light intensity and to achieve an optical system capable of preventing two or more cells from being coincidentally irradiated with a laser beam. Before reaching a sample stream containing cells, the laser beam passes through two first and second cylindrical collecting lenses to be focused to an elliptical cross-section. The first cylindrical collecting lens is provided to adjust the width of a laser beam, and the second cylindrical collecting lens is provided to adjust the height of a laser beam. The laser beam focused to an elliptical cross-section by passage through the two lenses irradiates a cell flowing through a slim flow cell having a rectangular cross-section. The sample stream becomes narrower by reducing the sample pressure, which makes it possible to allow a cell to pass through the center of a laser beam where fluctuations in light intensity are smaller, thereby improving measurement resolution.

However, the flow cytometer described in the aforementioned online article "Introduction to Principles of FCM-V" has a problem in that its measurement resolution cannot be improved to such an extent that intracellular local information such as proteins can be examined.

DISCLOSURE OF THE INVENTION

Problems to be Solved by the Invention

In order to solve the above problem, an object of the present invention is to provide a fluorescence detection device and a fluorescence detection method which are capable of improving measurement resolution to such an extent that intracellular local information such as proteins can be examined.

To solve the problems, the present invention provides a fluorescence detection device for measuring fluorescence emitted from a measurement object by irradiation with a laser beam, including:

a flow cell body including a flow channel through which a measurement object flows;

a laser light source unit that irradiates, with a laser beam, the measurement object passing through a measurement point in the flow channel;

a light-receiving unit that receives fluorescence emitted from the measurement object irradiated with the laser beam and outputs a light-reception signal; and a processing unit that outputs an output value of fluorescence intensity based on the light-reception signal outputted by the light-receiving unit, wherein the flow cell body has a lens provided on a surface thereof so as to traverse an optical path of the laser beam, and wherein when the lens is virtually cut along a plane including the measurement point of the measurement object and being perpendicular to a moving direction of the measurement object, the lens has a cross-section constituting a part of a circle of which center is located at the measurement point.

In the present invention, the lens is preferably a spherical lens which constitutes a part of a sphere and of which focal position corresponds to the measurement point.

Preferably, the flow channel provided in the flow cell body has a rectangular cross-section, and an optical axis of the laser beam, with which the measurement object is irradiated, is parallel with one side of the rectangular cross-section, and a ratio of a length of another side of the rectangular cross-section to a length of the one side of the rectangular cross-section is 1 to 2.5. Another side of the rectangular cross-section is perpendicular to the one side of the rectangular cross-section parallel with the optical axis of the laser beam.

In this case, the length of the one side of the rectangular cross-section parallel with the optical axis of the laser beam is preferably 30 to 200 times an average diameter of the measurement object.

The flow cell body and the lens are preferably made of the same material.

Also preferably, the flow cell body has another lens provided on a surface thereof in an optical path of the fluorescence between the measurement point and the light-receiving unit. Another lens has a cross-section constituting a part of a circle of which center is located at the measurement point.

The measurement object may be a cell, and a part of the cell may be irradiated with the laser beam at the measurement point and the light-receiving unit may receive fluorescence emitted from a protein contained in the cell.

To solve the problems, the present invention also provides a fluorescence detection method of measuring fluorescence emitted from a measurement object by irradiation with a laser beam, including the steps of:

allowing a measurement object to flow through a flow channel provided in a flow cell body;

irradiating the measurement object passing through a measurement point in the flow channel with a laser beam focused by a lens which is provided on a surface of the flow cell body and of which cross-section constitutes a part of a circle of which center is located at the measurement point, when the cross-section is obtained by virtually cutting along a plane including the measurement point of the measurement object and being perpendicular to a moving direction of the measurement object;

receiving fluorescence emitted from the measurement object irradiated with the laser beam to output a light-reception signal; and outputting an output value of fluorescence intensity based on the outputted light-reception signal.

In the present invention, the lens is preferably a spherical lens which constitutes a part of a sphere and of which focal position corresponds to the measurement point.

Effects of the Invention

The fluorescence detection device according to the present invention has a lens provided on the surface of a flow cell body having a flow channel through which a measurement object flows. When this lens is virtually cut along a plane including a measurement point of the measurement object and being perpendicular to the moving direction of the measurement object, the resulting cross-section of the lens constitutes a part of a circle of which center is located at the measurement point. Therefore, the numerical aperture (NA) of a focused laser beam can be made higher than ever before, thereby reducing the diameter of the focused laser beam. Particularly, the use of a spherical lens which constitutes a part of a sphere and of which focal position corresponds to the measurement point makes it possible to efficiently reduce the diameter of a focused laser beam.

Further, the fluorescence detection method according to the present invention using such a lens as described above also makes it possible to achieve a higher Numerical aperture (NA) of a focused laser beam than ever before, thereby reducing the diameter of the focused laser beam. Particularly, the use of a spherical lens which constitutes a part of a sphere and of which focal position corresponds to the measurement point makes it possible to efficiently reduce the diameter of a focused laser beam.

Therefore, according to the present invention, it is possible to improve measurement resolution to such an extent that intracellular local information such as proteins can be examined.

BEST MODE FOR CARRYING OUT THE INVENTION

Hereinbelow, a fluorescence detection device and a fluorescence detection method according to the present invention will be described in detail.

Figure 1:
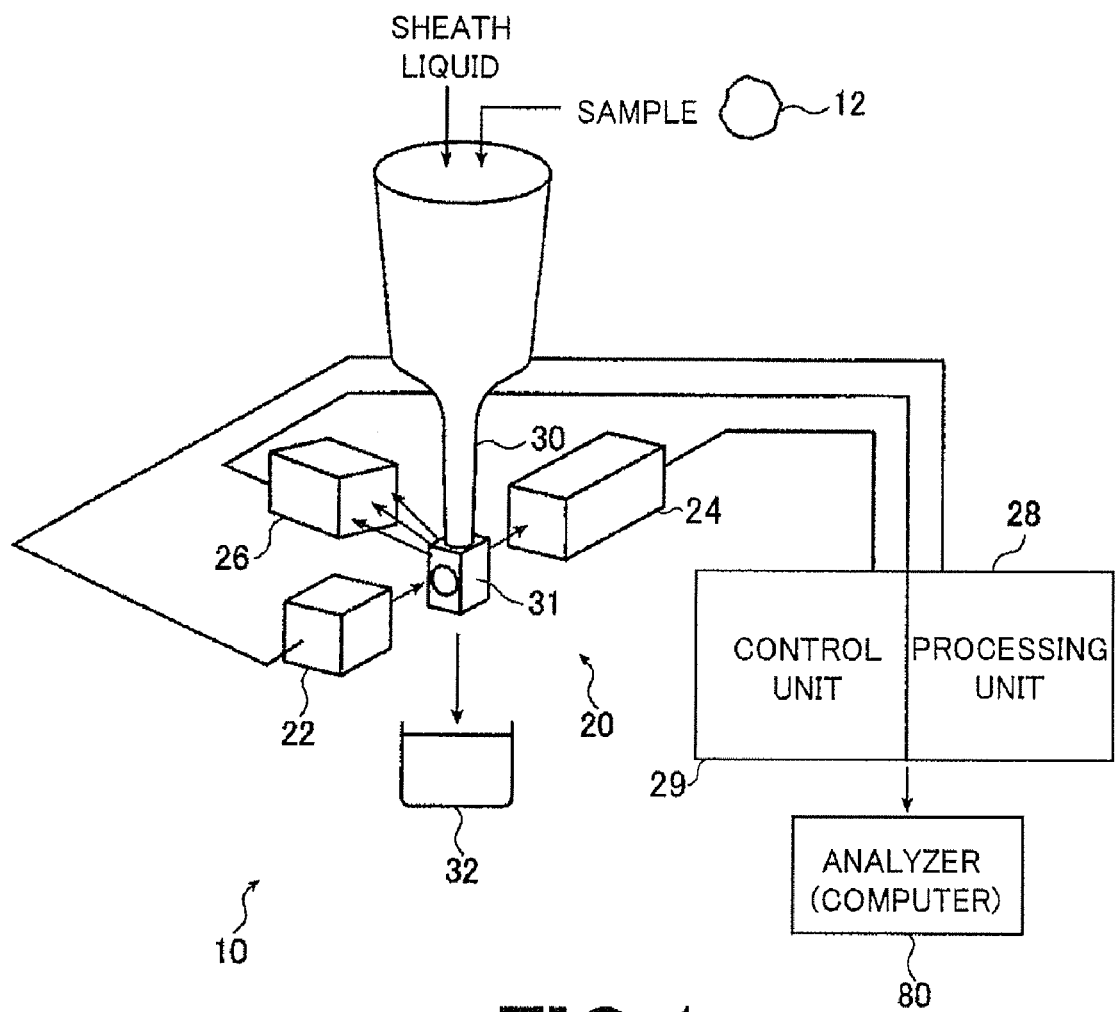
FIG. 1 is a schematic view illustrating the composition of a flow cytometer using a fluorescence detection device according to the present invention.

FIG. 1 is a schematic view illustrating the composition of a flow cytometer 10 using the fluorescence detection device according to the present invention.

The flow cytometer 10 includes a signal processor (fluorescence detection device) 20 and an analyzer 80. The signal processor 20 irradiates a sample 12 to be measured such as a cell with a laser beam to detect fluorescence emitted from part of the sample 12 such as a protein and performs signal processing. The analyzer 80 analyzes a measurement object contained in the sample 12 based on processing results obtained by the signal processor 20.

The signal processor 20 includes a laser light source unit 22, light-receiving units 24 and 26, a processing unit 28, a control unit 29, a tube 30 through which the sample 12 flows together with a sheath liquid that forms a high-speed stream, and a flow cell body 31. The processing unit 28 outputs an output value of intensity of fluorescence emitted from the sample 12. The control unit 29 allows the laser light source unit 22 to emit a laser beam at a predetermined intensity, and controls various processing operations performed by the processing unit 28. The flow cell body 31 is connected to the end of the tube 30 to form a flow of the sample 12. In the flow cell body 31, a laser irradiation point (measurement point) is provided in a flow channel of the sample 12. On the output side of the flow cell body 31, a recovery container 32 is provided. The flow cytometer 10 may be provided with a cell sorter for separating specific cells or the like contained in the sample 12 in a short period of time after irradiation with a laser beam. In this case, two or more recovery containers are provided to collect separated cells.

The laser light source unit 22 emits three beams of laser light having different wavelengths (e.g., $\lambda_1$=405 nm, $\lambda_2$=533 nm, $\lambda_3$=650 nm). The laser beams are focused by a lens system on a predetermined position in the flow channel of the flow cell body 31. The focus position corresponds to the measurement point of the sample 12.

Figure 2:
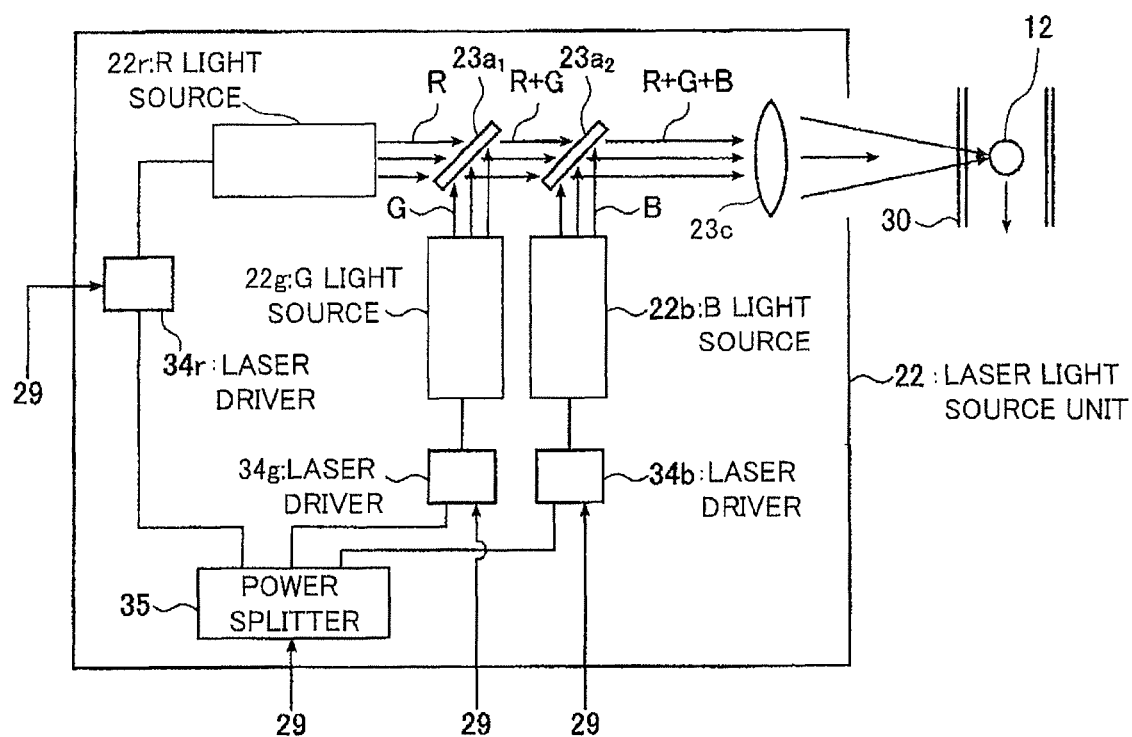
FIG. 2 is a schematic view illustrating the composition of one example of a laser light source unit used in the fluorescence detection device according to the present invention.

FIG. 2 is a schematic view illustrating one example of the composition of the laser light source unit 22.

The laser light source unit 22 includes an R light source 22r, a G light source 22g, a B light source 22b, dichroic mirrors $23a_1$ and $23a_2$, a lens system 23c, laser drivers 34r, 34g, and 34b, and a power splitter 35.

Each of the R light source 22r, the G light source 22g, and the B light source 22b emits a laser beam having a visible wavelength of 350 nm to 800 nm. The R light source 22r mainly emits a red laser beam R at a predetermined intensity. The G light source 22g emits a green laser beam G at a predetermined intensity. The B light source 22b emits a blue laser beam B at a predetermined intensity.

Each of the dichroic mirrors $23a_1$ and $23a_2$ transmits a laser beam having a specific wavelength band but reflects a laser beam having a wavelength band other than the specific wavelength band.

The lens system 23c focuses a laser beam comprising the laser beams R, G, and B on the measurement point in the tube 30. The laser drivers 34r, 34g, and 34b drive the R light source 22r, the G light source 22g, and the B light source 22b, respectively.

The power splitter 35 distributes a supplied signal to the laser drivers 34r, 34g, and 34b.

Each of the light sources 22r, 22g, and 22b that emits a laser beam can be composed of, for example, a semiconductor laser.

The dichroic mirror $23a_1$ is a mirror that transmits the laser beam R but reflects the laser beam G. The dichroic mirror $23a_2$ is a mirror that transmits the laser beam R and the laser beam G but reflects the laser beam B.

Such a configuration as described above makes it possible to combine the laser beams R, G, and B into an irradiation beam with which the sample 12 passing through the measurement point is irradiated.

The laser drivers 34r, 34g, and 34b are connected to the processing unit 28 and the control unit 29 and are configured to adjust the intensities of the laser beams R, G, and B.

The R light source 22r, the G light source 22g, and the B light source 22b oscillate at predetermined wavelength bands so that the laser beams R, and B can excite fluorochromes and the fluorochromes can emit fluorescence having specific wavelength bands. The fluorochromes excited by the laser beams R, G, and B are attached to the sample 12 to be measured such as a biological material. Therefore, when the sample 12 to be measured passes through the measurement point in the flow cell body 31, the fluorochromes are irradiated with the laser beams R, G, and B at the measurement point and emit fluorescence at specific wavelengths.

The light-receiving unit 24 is provided on the opposite side of the flow cell body 31 from the laser light source unit 22. The light-receiving unit 24 is equipped with a photoelectric converter that detects forward-scattered laser light from the sample 12 passing through the measurement point and outputs a detection signal informing the passage of the sample 12 through the measurement point. The signal outputted from the light-receiving unit 24 is supplied to the processing unit 28 and is used in the processing unit 28 as a trigger signal informing the timing of passage of the sample 12 through the measurement point in the tube 30.

On the other hand, the light-receiving unit 26 is arranged in a direction perpendicular to the emission direction of a laser beam emitted from the laser light source unit 22 and to the moving direction of the sample 12 flowing through the flow channel of the flow cell body 31. The light-receiving unit 26 is equipped with a photoelectric converter that receives fluorescence emitted from the sample 12 irradiated with a laser beam at the measurement point.

Figure 3:
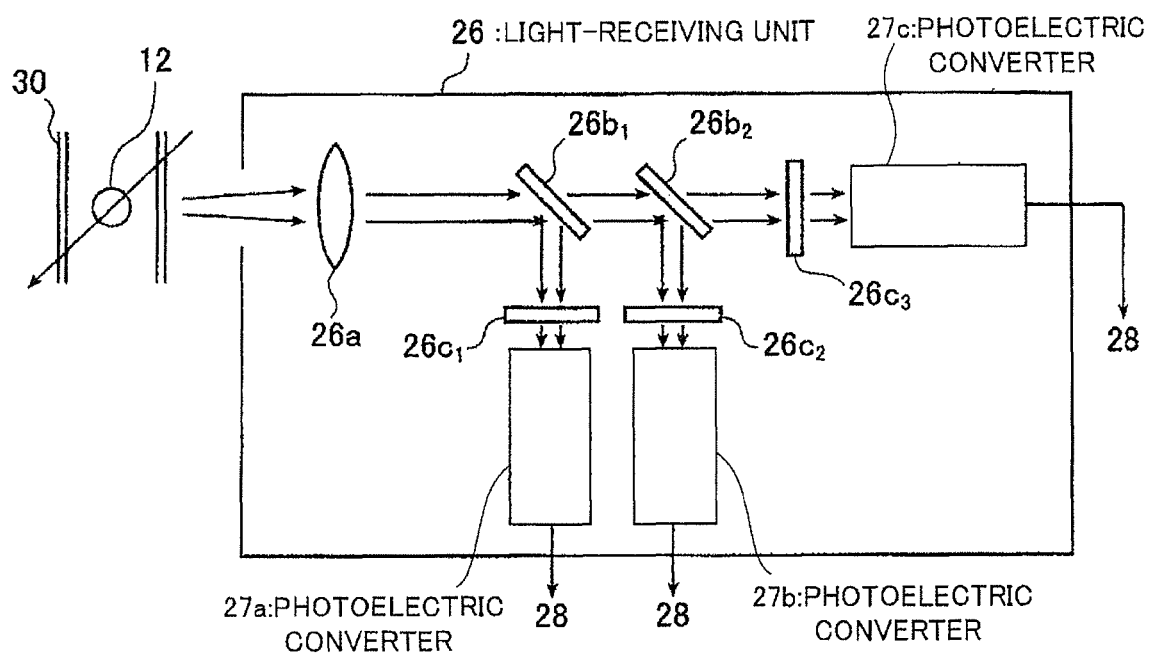
FIG. 3 is a schematic view illustrating the composition of one example of a light-receiving unit used in the fluorescence detection device according to the present invention.

FIG. 3 is a schematic view illustrating the composition of one example of the light-receiving unit 26.

The light-receiving unit 26 shown in FIG. 3 includes a lens system 26a that focuses a fluorescence signal from the sample 12, dichroic mirrors $26b_1$ and $26b_2$, band pass filters $26c_1$ to $26c_3$, and photoelectric converters 27a to 27c such as photoelectric multiplier tubes.

The lens system 26a is configured to focus fluorescence incident on the light-receiving unit 26 onto light-receiving surfaces of the photoelectric converters 27a to 27c.

The dichroic mirrors $26b_1$ and $26b_2$ is a mirror that reflects fluorescence having a predetermined wavelength band but transmits other fluorescence. The reflection wavelength bands and transmission wavelength bands of the dichroic mirrors $26b_1$ and $26b_2$ are set so that fluorescence having predetermined wavelength bands can be received by the photoelectric converters 27a to 27c by filtering using the band pass filters $26c_1$ to $26c_3$.

Each of the band pass filters $26c_1$ to $26c_3$ is a filter that transmits only fluorescence having a predetermined wavelength band, and is provided in front of the light-receiving surface of each of the photoelectric converters 27a to 27c. The wavelength bands of fluorescence that can pass through the band pass filters $26c_1$ to $26c_3$ are set so as to correspond to the wavelength bands of fluorescence emitted from the fluorochromes.

Each of the photoelectric converters 27a to 27c is a sensor equipped with, for example, a photoelectric multiplier tube, and converts light received by its photoelectric surface into an electric signal.

The control unit 29 is a unit that allows the laser light source unit 22 to emit a laser beam at a predetermined intensity and controls various processing operations performed by the processing unit 28.

The processing unit 28 is a unit that performs predetermined signal processing to output an output value of fluorescence intensity to the analyzer 80.

The analyzer 80 is a device that identifies, for example, the type of a biological material contained in the sample 12 passing through the measurement point in the flow cell body 31 based on the output value supplied from the processing unit 28 and analyzes the biological material contained in the sample 12. In this way, the analyzer 80 determines, for example, a histogram of a biological material contained in the sample 12 or various characteristics of a biological material contained in the sample 12 in a short period of time.

Figure 4A:
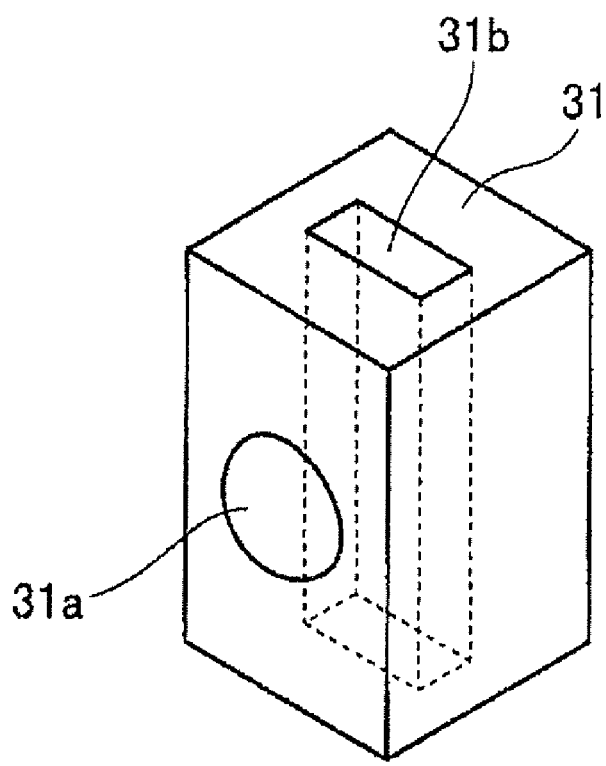
FIGS. 4(a) and 4(b) are illustrations for explaining a flow cell body used in the fluorescence detection device according to the present invention.
Figure 4B:
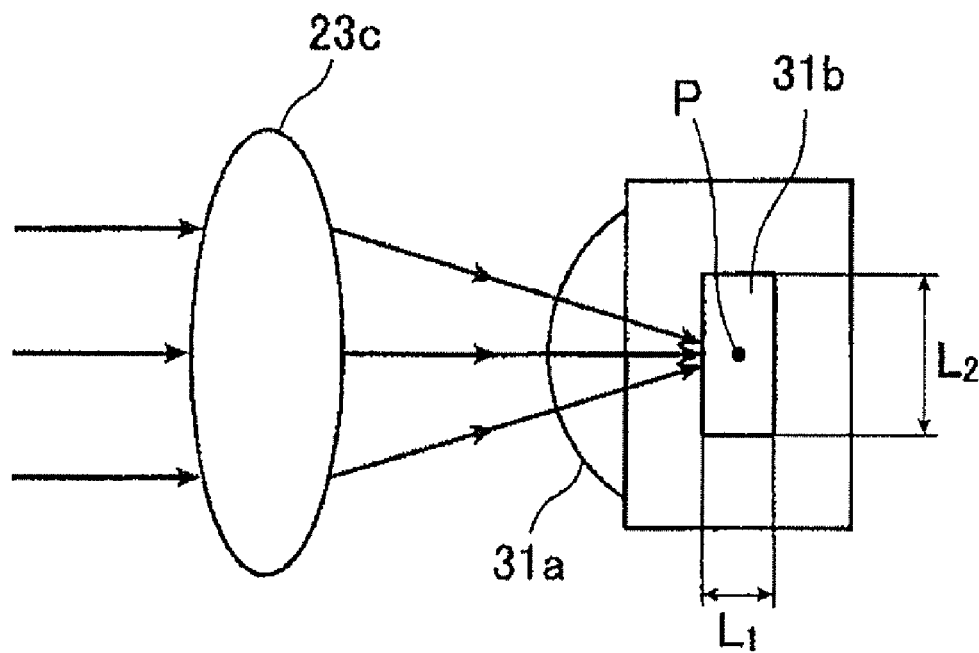

The lower end of the tube 30 is connected to the flow cell body 31. The flow cell body 31 is characteristic in the present invention. FIG. 4(a) is a schematic perspective view of the flow cell body 31, and FIG. 4(b) is an illustration for explaining a state where a laser beam enters the flow cell body 31.

The flow cell body 31 is a rectangular parallelepiped transparent member made of, for example, quartz. A laser beam enters the flow cell body 31 through its side surface, travels inside the flow cell body 31, and is focused on the center of a flow channel 31b extending from the tube 30 in the longitudinal direction. The focus position corresponds to a measurement point P. The measurement point P is located on a focal position of the lens system 23c of the laser light source unit 22.

On the side surface of the flow cell body 31 through which a laser beam enters the flow cell body 31, there is provided a spherical lens 31a which constitutes a part of a sphere and of which focal position corresponds to the measurement point P. More specifically, the spherical lens 31a is provided so as to traverse the optical path of a laser beam. The center of the sphere including the spherical lens 31a, that is, the center of curvature of the spherical lens 31a corresponds to the measurement point P of the sample 12. The reference numeral 23c in FIG. 4(b) denotes the lens system (focusing lens) of the laser light source unit 22 illustrated in FIG. 2. The spherical lens 31a is made of the same material as the flow cell body 31, for example, quartz.

The reason why the spherical lens 31a is provided on the laser beam incidence plane of the flow cell body 31 is to reduce the diameter of a focused laser beam to improve measurement resolution.

In a case where the spherical lens 31a is provided on the flow cell body 31, a laser beam which has passed through the lens system 23c enters the spherical lens 31a at an incident angle of 0° and is focused on the measurement point P. In this case, the Numerical aperture (NA) of a focused laser beam incident on the flow cell body 31 is improved as compared to a case where the spherical lens 31a is not provided.

Figure 5:
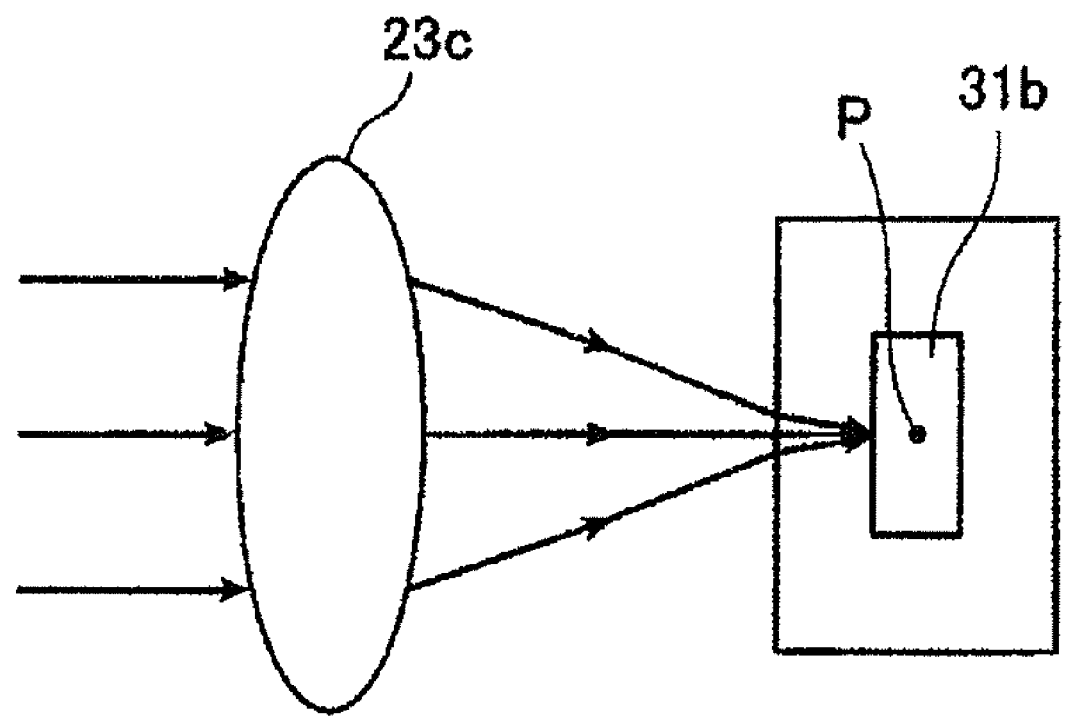
FIG. 5 is an illustration for explaining a state where a laser beam enters a conventional flow cell body.

More specifically, the NA of a focused laser beam incident on the flow cell body 31 can be represented by the formula: (refractive index of medium)×sin θ, wherein θ is an incident angle of a laser beam on the flow cell body 31. In a case where the spherical lens 31a is provided on the flow cell body 31, θ is not changed because a laser beam that has passed through the lens system 23c always enters the spherical lens 31a at an incident angle of 0°. In this case, the NA of a focused laser beam that has passed through the spherical lens 31a is a value determined by the formula: refractive index of medium×sin θ. On the other hand, as shown in FIG. 5, in a case of a conventional flow cell body not having the spherical lens 31a, the incident angle of a laser beam on the side surface of the flow cell body 31 is not 0° except for the optical axis of the laser beam. In this case, according to the Snell laws of refraction, the NA of a focused laser beam incident on the flow cell body 31 is a value of sin θ. Unlike such a conventional flow cell body, the flow cell body 31 of the fluorescence detection device 20 according to the present invention has the spherical lens 31a to prevent the NA of a focused laser beam from being reduced at a surface of the flow cell body 31 at the time when the laser beam enters the flow cell body 31.

By providing the spherical lens 31a, the NA of a focused laser beam can be made higher than ever before according to the following formula, thereby reducing the diameter of the focused laser beam. The following formula is derived assuming that a laser beam has a Gaussian distribution.

Diameter $\epsilon$ of focused laser beam=$4\times\lambda\times f/(\pi D)=0.64\lambda/NA$, where $\lambda$ is the wavelength of a laser beam, f is the focal length of a lens, and D is the opening size of the lens system 23c.

As described above, by providing the spherical lens 31a on the side surface of the flow cell body 31 where a focused laser beam enters, it is possible to reduce the diameter of the focused laser beam, thereby improving measurement resolution to such an extent that intracellular local information such as proteins can be examined.

It is to be noted that in this embodiment, the spherical lens 31a is provided on one side surface of the flow cell body 31 having a rectangular parallelepiped shape, but in order to improve fluorescence measurement resolution of the light-receiving unit 26, the spherical lens 31 may be provided on another side surface of the flow cell body 31 through which fluorescence passes into the light-receiving unit 26. Also in this case, the spherical lens 31 is arranged in such a manner that the focal position of the spherical lens 31 corresponds to the measurement point P.

In the present invention, the NA of a focused laser beam is made higher than ever before in order to reduce the size of the focused laser beam. For this purpose, as described above, the spherical lens 31a is provided on the side surface of the flow cell body 31. However, as represented by the following formula, an increase in the NA of a focused laser beam reduces the depth of focus, which may reduce measurement resolution.

$$\text{Depth of focus } z=0.64/(NA)^2$$

Therefore, in the present invention, the cross-sectional shape of the flow channel 31b formed in the flow cell body 31 is preferably limited to the following.

As illustrated in FIG. 4(b), the cross-section of the flow channel 31b formed in the flow cell body 31 has a rectangular shape so that the optical axis of a laser beam emitted from the laser light source unit 22 is parallel with one side of the rectangular cross-section of the flow channel 31b. When the length of one side of the rectangular cross-section of the flow channel 31b parallel with the optical axis of a laser beam is defined as $L_1$ and the length of another side of the rectangular cross-section of the flow channel 31b perpendicular to the one side of the rectangular cross-section of the flow channel 31b is defined as $L_2$, the ratio of $L_2$ to $L_1$ is 1 to 2.5. By setting the ratio of $L_2/L_1$ of the rectangular cross-section of the flow channel 31b to a value within the above range, it is possible to regulate the position of the sample 12 in the direction of the optical axis of a laser beam when the sample 12 passes through the laser beam. That is, the disadvantage of a reduction in the depth of focus caused by an increase in NA can be overcome by regulating the position of the sample 12 flowing through the flow channel 31b by setting the ratio of $L_2/L_1$ of the rectangular cross-section of the flow channel 31b to 1 to 2.5. Further, the length $L_1$ is preferably 30 to 200 times the average size (diameter) of the sample 12 to be measured.

The flow cytometer 10 has the above-described composition.

In such a flow cytometer 10 having the flow cell body 31, fluorescence emitted from the sample 12 by irradiation with a laser beam is measured by the following fluorescence detection method.

The sample 12 is allowed to flow through a flow channel provided in the flow cell body 31 together with a sheath liquid. Then, when passing through a measurement point in the flow channel, the sample 12 is irradiated with a laser beam focused by the spherical lens 31a provided on the surface of the flow cell body 31. The spherical lens 31a is a lens of which a cross-section constitutes a part of a circle of which center is located at the measurement point, when the cross-section is obtained by virtually cutting along a plane including the measurement point of the sample 12 and being perpendicular to the moving direction of the sample 12. Fluorescence emitted from the sample 12 irradiated with a laser beam is received and a light-reception signal is outputted. Based on the outputted light-reception signal, an output value of fluorescence intensity is outputted.

It is to be noted that the spherical lens 31 constitutes a part of a sphere and the focal position of the spherical lens 31a corresponds to the measurement point.

It is to be noted that, in this embodiment, the spherical lens 31a is provided on the flow cell body 31, but the present invention is not limited to this embodiment. A lens to be provided on the laser beam incidence surface of the flow cell body 31 is not particularly limited as long as its cross section, which is obtained by virtually cutting along a plane including the measurement point P of the sample 12 and being perpendicular to the moving direction of the sample 12, constitutes a part of a circle. For example, a cylindrical lens may be used.

Although the fluorescence detection device and the fluorescence detection method according to the present invention have been described above in detail, the present invention is not limited to the above embodiment, and various changes and modifications may be made without departing from the scope of the present invention.

What is claimed is:

1. A fluorescence detection device for measuring fluorescence emitted from a measurement object by irradiation with a laser beam, comprising:
    a flow cell body including a flow channel through which a measurement object flows;
    a laser light source unit that irradiates, with a laser beam, the measurement object passing through a measurement point in the flow channel;
    a light-receiving unit that receives fluorescence emitted from the measurement object irradiated with the laser beam and outputs a light-reception signal; and
    a processing unit that outputs an output value of fluorescence intensity based on the light-reception signal outputted by the light-receiving unit,
    wherein the flow cell body has a lens provided on a surface thereof so as to traverse an optical path of the laser beam, and wherein when the lens is virtually cut along a plane including the measurement point of the measurement object and being perpendicular to a moving direction of the measurement object, the lens has a cross-section constituting a part of a circle of which center is located at the measurement point.

2. The fluorescence detection device according to claim 1, wherein the lens is a spherical lens which constitutes a part of a sphere and of which focal position corresponds to the measurement point.

3. The fluorescence detection device according to claim 1, wherein the flow cell body and the lens are made of the same material.

4. The fluorescence detection device according to claim 1, wherein the flow cell body has another lens provided on a surface thereof in an optical path of the fluorescence between the measurement point and the light-receiving unit, and wherein said another lens has a cross-section constituting a part of a circle of which center is located at the measurement point.

5. The fluorescence detection device according to claim 1, wherein the measurement object is a cell, and wherein a part of the cell is irradiated with the laser beam at the measurement point and the light-receiving unit receives fluorescence emitted from a protein contained in the cell.

6. The fluorescence detection device according to claim 1, further comprising a focus lens which focuses the laser beam on the measurement point such that a part of the measurement object is irradiated with the focused laser beam, and the light-reception signal is a signal of fluorescence which is emitted by the part of the measurement object.

7. The fluorescence detection device according to claim 1, further comprising a focusing lens provided between the laser light source and the flow cell body, to focus the laser beam on the measuring point with the lens provided on the surface of the flow cell body.

8. A fluorescence detection device for measuring fluorescence emitted from a measurement object by irradiation with a laser beam, comprising:
a flow cell body including a flow channel through which a measurement object flows;
a laser light source unit that irradiates, with a laser beam, the measurement object passing through a measurement point in the flow channel;
a light-receiving unit that receives fluorescence emitted from the measurement object irradiated with the laser beam and outputs a light-reception signal; and
a processing unit that outputs an output value of fluorescence intensity based on the light-reception signal outputted by the light-receiving unit,
wherein the flow cell body has a lens provided on a surface thereof so as to traverse an optical path of the laser beam, and wherein when the lens is virtually cut along a plane including the measurement point of the measurement object and being perpendicular to a moving direction of the measurement object, the lens has a cross-section constituting a part of a circle of which center is located at the measurement point,
wherein the flow channel provided in the flow cell body has a rectangular cross-section, and wherein an optical axis of the laser beam, with which the measurement object is irradiated, is parallel with one side of the rectangular cross-section, and wherein a ratio of a length of another side of the rectangular cross-section to a length of the one side of the rectangular cross-section is 1 to 2.5, said another side of the rectangular cross-section being perpendicular to the one side of the rectangular cross-section parallel with the optical axis of the laser beam.

9. The fluorescence detection device according to claim 8, wherein the length of the one side of the rectangular cross-section parallel with the optical axis of the laser beam is 30 to 200 times an average diameter of the measurement object.

10. A fluorescence detection method of measuring fluorescence emitted from a measurement object by irradiation with a laser beam, comprising the steps of:
allowing a measurement object to flow through a flow channel provided in a flow cell body;
irradiating the measurement object passing through a measurement point in the flow channel with a laser beam focused by a lens which is provided on a surface of the flow cell body and of which cross-section constitutes a part of a circle of which center is located at the measurement point, when the cross-section is obtained by virtually cutting along a plane including the measurement point of the measurement object and being perpendicular to a moving direction of the measurement object;
receiving fluorescence emitted from the measurement object irradiated with the laser beam to output a light-reception signal; and
outputting an output value of fluorescence intensity based on the outputted light-reception signal.

11. The fluorescence detection method according to claim 10, wherein the lens is a spherical lens which constitutes a part of a sphere and of which focal position corresponds to the measurement point.

12. The fluorescence detection method according to claim 10, wherein a part of the measurement object is irradiated with the focused laser beam and the received fluorescence is light which is emitted by the part of the measurement object.

13. The fluorescence detection method according to claim 10, wherein the laser beam is focused by a focusing lens provided between the laser light source and the flow cell body, to focus the laser beam on the measuring point with the lens provided on the surface of the flow cell body.

* * * * *